United States Patent [19]

Hancock et al.

[11] 4,090,878
[45] May 23, 1978

[54] ARRANGEMENT FOR PREPARING NATURAL TISSUE FOR IMPLANTATION

[75] Inventors: Warren D. Hancock, Newport Beach; Frederick P. Sattler, Fullerton, both of Calif.

[73] Assignee: Hancock Laboratories, Inc., Anaheim, Calif.

[21] Appl. No.: 835,522

[22] Filed: Sep. 22, 1977

Related U.S. Application Data

[60] Division of Ser. No. 665,520, Mar. 10, 1976, Pat. No. 4,050,893, which is a continuation of Ser. No. 490,686, Jul. 22, 1974, abandoned, which is a continuation-in-part of Ser. No. 324,217, Jan. 16, 1973, abandoned, which is a continuation of Ser. No. 28,630, Apr. 15, 1970, abandoned.

[51] Int. Cl.² .............................................. C14C 15/00
[52] U.S. Cl. ...................................................... 69/29
[58] Field of Search .................... 69/21, 29; 8/94.11; 128/274; 3/1, 1.2, 1.4, 1.5

[56] References Cited

U.S. PATENT DOCUMENTS

| 101,661 | 4/1870 | Robertson | 69/29 |
| 816,670 | 4/1906 | Marneffe | 69/29 |
| 2,648,079 | 8/1953 | Ushakoff | 69/21 X |
| 3,966,401 | 6/1976 | Hancock et al. | 8/94.11 |
| 3,988,782 | 11/1976 | Dardik et al. | 3/1 |
| 4,050,893 | 9/1977 | Hancock et al. | 8/94.11 |

Primary Examiner—Alfred R. Guest
Attorney, Agent, or Firm—Gausewitz, Carr & Rothenberg

[57] ABSTRACT

An arrangement for preparing natural tissue in the form of a heart valve, vessel or the like for implantation in which tanning fluid under pressure is applied to a portion of the tissue so as to cause said tissue to assume substantially its natural configuration, while additional tanning fluid is applied to the remainder of the tissue, said tanning fluid being so applied for a time sufficient to cause the tissue to become fixed, and, for vessels or the like, a guide may engage the tissue during fixation, whereby said tissue maintains substantially the configuration of the guide.

10 Claims, 9 Drawing Figures

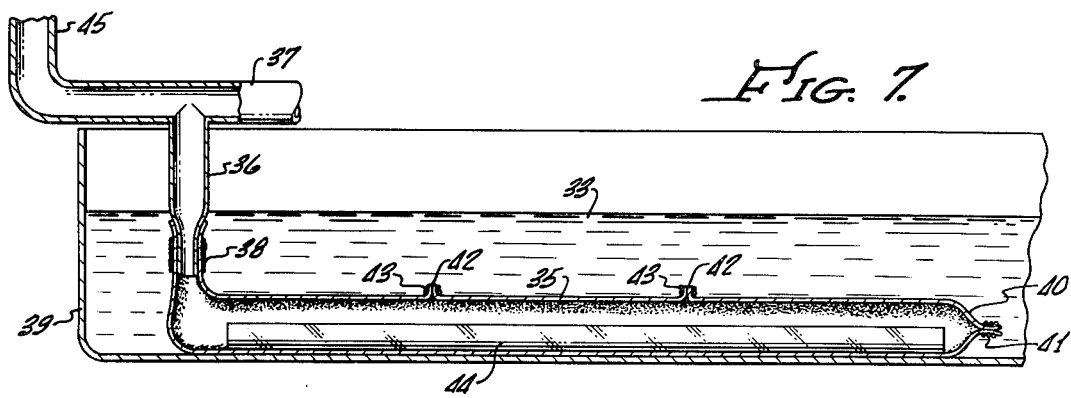
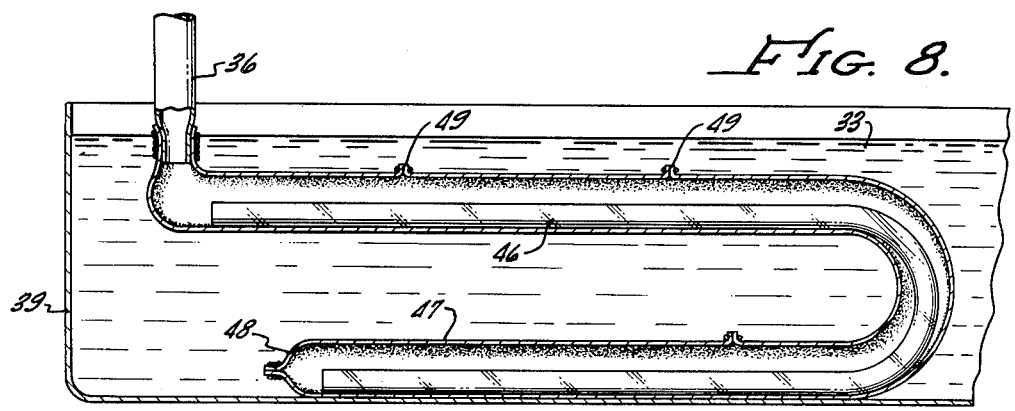
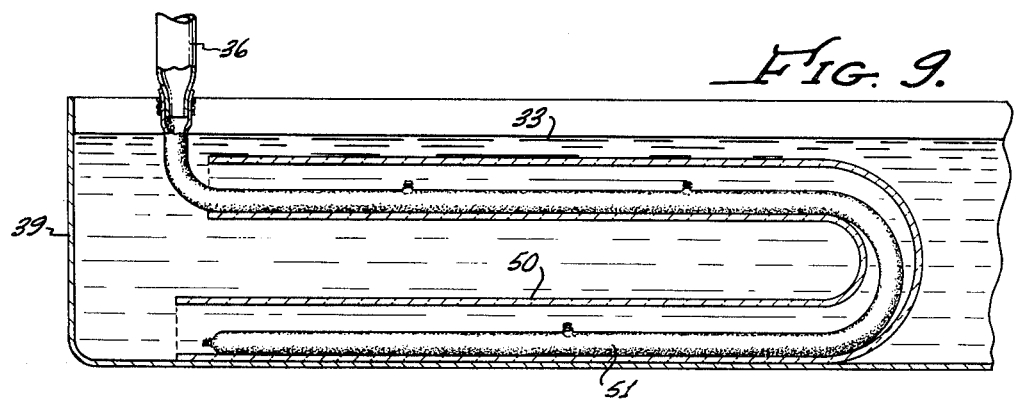
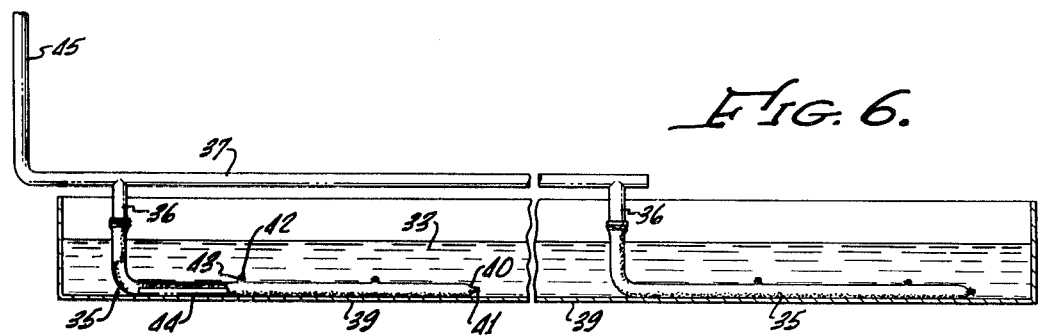

ARRANGEMENT FOR PREPARING NATURAL TISSUE FOR IMPLANTATION

REFERENCE TO RELATED APPLICATIONS

This is a division of pending patent application Ser. No. 665,520, filed Mar. 10, 1976, which issued as U.S. Pat. No. 4,050,893 on Sept. 9, 1977 which is a continuation of patent application Ser. No. 490,686, filed July 22, 1974, now abandoned, which was a continuation-in-part of our application Ser. No. 324,217, filed Jan. 16, 1973, now abandoned, which was a continuation of patent application Ser. No. 28,630, filed Apr. 15, 1970, now abandoned.

BACKGROUND OF THE INVENTION

1. Field of the Invention

This invention relates to the preparation of natural tissue for implantation.

2. Description of Prior Art

Natural aortic valves taken from animals or humans have been used for a number of years for allo and xenograft replacement of diseased valves. This has experienced only limited success, however, as in a large proportion of cases the replacement valves develop leakage. The incidence of incompetency has run from 40 to 80%. This occurs primarily because the valve is a very flexible and elastic structure which does not maintain its normal physiologic state when removed from the donor heart. This readily distortable element must then be matched with the flexible structure of the patient's heart, which also is not in its normal physiologic state when prepared for the valve replacement. With distortion of the flexible valve being unavoidable, and with no two valves being the same, it becomes virtually impossible to affix the valve to a stent or the patient's annulus at the proper location to maintain the valve's natural configuration. Consequently, undesirable stresses are introduced into the valve. This may result in immediate incompetence of the valve. Even where this does not prevent competence initially, the existence of the stresses in the valve over a period of time frequently causes premature failure.

If an appropriate tanning fluid is applied to a natural heart valve, its tissue becomes fixed so that it loses its characteristic of extreme flexibility and elasticity. As a result, in order to assure retention of approximately normal geometry, the cusps of the allo and xenograft valves have been packed with cotton, and the valves then have been fixed by tanning. This, however, has not solved the problem of valve failure because it never has been possible to impart exactly its natural configuration to a valve by packing it with cotton or similar material. Consequently, there are inevitably variations from the normal valve shape, and these differences become fixed in the valve by the tanning operation. These shape variations introduce stresses in the valve, which may cause it to fail subsequently.

Another problem encountered from such tanning of the valve is that shrinkage occurs as a result of this procedure. The amount of shrinkage is not the same in different valves, so that there is no way of predicting how much shrinkage will take place. Later, when the valve is exposed to biologic fluid after it has been implanted, it experiences some re-expansion. Again, this is an unknown amount. These factors contribute to the difficulty in properly mounting the valve and make the introduction of undesirable stresses practically unavoidable.

Similar problems have been encountered with vessels which also have been prepared for implantation by fixation with a tanning fluid. Problems have included inadequate penetration of the fixative, a lack of uniformity of fixation and insufficient tensile strength in the prepared vessels.

SUMMARY OF THE INVENTION

The present invention overcomes the difficulties previously encountered with natural valves, vessels and the like. It permits a natural heart valve to be fixed in its natural state so that it will retain its shape and can be readily and correctly mounted on a stent or affixed directly to the annulus of the heart of the patient. By this procedure, the valve is subjected to fluid pressure and at the same time fixed by exposure to a tanning fluid. It has been found that, when fluid pressure is applied to a valve after removal from the heart, the valve will be given its natural shape. Therefore, when fixed in a pressurized condition, the valve will retain its normal architecture, allowing proper mounting to be achieved. Similarly, vessels are subjects to pressure while being fixed with comparable improved results.

The valve may be pressurized by introducing the tanning fluid into it while subjecting the exterior of the valve to a bath of the same tanning fluid. In accomplishing this, the valve and associated ascending aorta are excised from the donor heart and attached to a stopper which has an opening through it. The tanning fluid is introduced through this opening into the interior of the valve, and a normal physiologic pressure is applied. This may be accomplished accurately by providing a source of the tanning fluid at a predetermined height with respect to the valve, so that the pressure head on the valve is at the correct value. After an appropriate period in the tanning solution, the valve is fixed in its natural contour and, upon removal, will retain this shape. Then, upon trimming, it is ready for mounting on a stent or for attachment to the heart of the patient. The prepared valve also may be stored frozen for future use or stored in the solution.

When fixed under pressure in this manner, the valve does not shrink during the tanning process, nor does undesirable expansion occur subsequently when the valve is subjected to the biologic fluid. The tanning process takes place more rapidly when the tanning solution is under pressure. Also, when tanned under pressure, the tensile strength of the tissue of the valve becomes increased. Improved results are obtained additionally because, when subjected to the pressure of the tanning fluid, valves that inherently will leak may be detected through the loss of fluid through the valve. These may be discarded so that only properly functioning valves will be retained for subsequent implantation.

In preparing a vessel, the collaterals and one end are ligated, and the other end is attached to a source of pressurized tanning fluid. While the interior of the vessel is subjected to the pressurized tanning fluid, the exterior is submersed in a bath of the tanning fluid. The natural overall contour of the vessel may be maintained as it is fixed by engaging it with a guide having the same general shape as the natural vessel contour. The guide also may impart a different contour to the vessel so that special shapes can be produced. The guide may be a rod received within the vessel or a tube surrounding the vessel.

BRIEF DESCRIPTION OF THE DRAWING

FIG. 6 is a side elevational view, partially in section, illustrating the arrangement for fixing vessels for implantation, utilizing straight rods for maintaining the configurations of the vessels;

FIG. 7 is an enlarged fragmentary view of a portion of the arrangement of FIG. 6, the vessel being shown internally pressurized;

FIG. 8 is a view similar to FIG. 7 but of a vessel receiving a curved rod as a guide member, with the vessel shown pressurized; and FIG. 9 is a view similar to FIGS. 7 and 8, but with a tube used to guide the vessel, and with the vessel shown unpressurized.

DESCRIPTION OF THE PREFERRED EMBODIMENT

Figures 1, 2, 3, 4, 5:
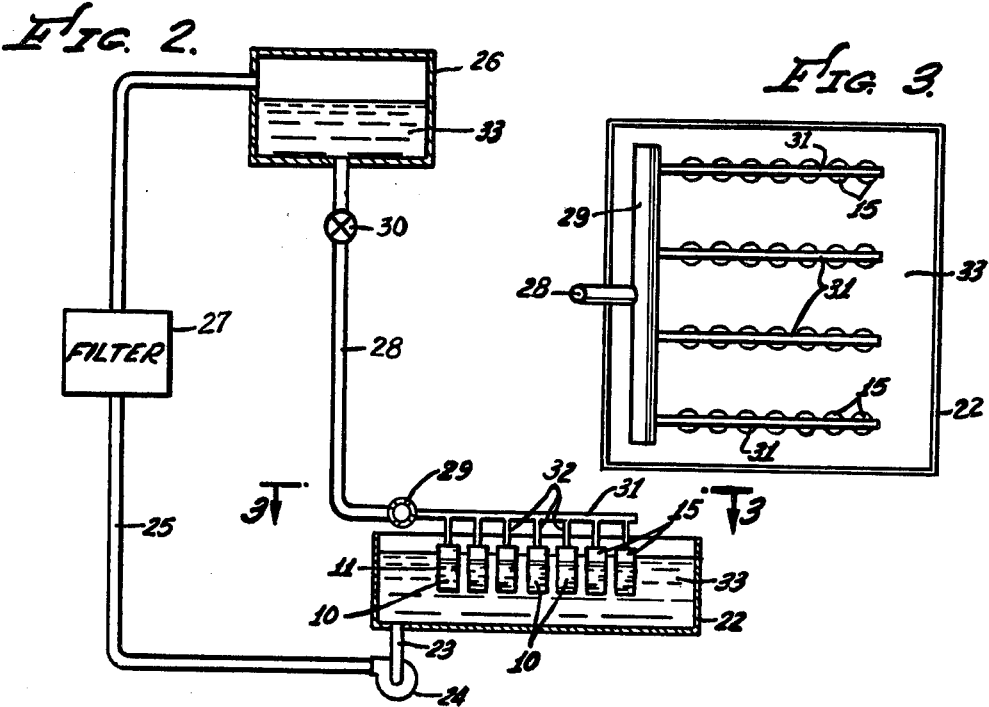
FIG. 1 is a longitudinal sectional view of a valve structure attached to a device for applying pressurized tanning fluid and after being fixed by the tanning fluid.
FIG. 2 is an elevational view, partially in section, illustrating an arrangement for treating a number of valves.
FIG. 3 is a top plan view showing the manifolding arrangement for distributing the tanning fluid.
FIG. 4 is a sectional view taken along line 4—4 of FIG. 1.
FIG. 5 is a view similar to FIG. 4 but illustrating the appearance of a valve in the absence of treatment in accordance with this invention.

In preparation for a transplant, an aortic valve 10 is excised along with the ascending aorta 11 and extraneous tissue removed. This includes removal of the aorta above the sinus of the Valsalva, the annulus and subvalvular structure. The coronary arteries 12 are ligated by sutures 13. The aorta 11 then is extended around a rubber stopper 15, which has a central axially extending opening 16 through it. The stopper 15, therefore, is positioned in the aorta 11 above the valve 10, between the valve and the arch of the aorta. A suture 17 is wrapped around the exterior to affix the aorta to the stopper 15. The result is the formation of a chamber 19 within the valve structure, closed at its lower end by the cusps 20 of the valve. Access to the upper portion of the chamber 19 is provided by the opening 16 through the stopper 15. This allows pressurized tanning fluid to be introduced into the chamber 19 to fix the valve 10 in its natural configuration.

In order to pressurize the valve, the arrangement shown in FIGS. 2 and 3 may be employed, which provides a means for treating a number of valves simultaneously. This system includes an open-topped tank 22 from the bottom of which extends a line 23 to a pump 24. The latter, through a conduit 25, connects to a reservoir 26 that is located above the tank 22. A filter 27 in the line 25 will remove any impurities in fluid conducted through the line 25 to the reservoir 26. Extending downwardly from the reservoir 26 is a line 28, the lower end of which connects to a main manifold 29. A shutoff valve 30 may be included in the line 28. Additional and smaller manifolds 31 extend outwardly from the main manifold 29, each of these being provided with a plurality of downwardly extending stems 32. The openings 16 of stoppers 15 to which valve elements have been attached receive the open lower ends of the stems 32. This positions the valve structures 10 within the tank 22.

A suitable tanning fluid 33, such as formaldehyde, glutaraldehyde or other aldehyde, is introduced into the tank 22 and the reservoir 26. The fluid 33 in the tank 22 covers the exteriors of the valve structures 10. This causes the upstream ends of the valves 10 to be submerged in the tanning fluid 33.

The fluid 33 from the reservoir 26 fills the interior chambers 19 of the valves 10, where it is retained by the cusps 20. Because the reservoir 26 is elevated with respect to the location of the valves 10, a static pressure head is developed which causes the tanning fluid in the chambers 19 to exert pressure against each of the valves 10. This fluid pressure applied from the proximal aorta, being thus on the downstream side of the valve 10, inflates the valve and causes the valve to assume its natural contour. The maximum elevation of the fluid 33 in the reservoir 26 is kept at a height to produce a pressure head such that the valves will be pressurized within the physiologic range. This is from 80 to 120 mm Hg, with 80 mm Hg being used most frequently as the pressurizing value. The pressurization is controlled accurately and changed as needed by selecting an appropriate elevation of the reservoir 26 over the tank 22 to result in a desired pressure head. This pressure is maintained within the chambers 19 of the valve structures for a period sufficient to attain a fixation of the tissue of the valves. In a 4% formaldehyde solution or a 0.2% glutaraldehyde solution, this will occur in around 72 hours.

After being maintained under fluid pressure in the presence of the tanning fluid, the valve is removed and then may be handled without disturbing its natural geometry. It is then ready for mounting on a stent or for being affixed in the annulus of the heart of a patient. The natural shape of the valve may be maintained without difficulty as it is mounted, because any distortion is visually apparent. The valve will keep its shape when prepared in this manner, exhibiting neither shrinkage from the preparation nor expansion from subsequent contact with biologic fluid. The chance of incompetence, even after a prolonged period of subsequent use, is greatly reduced. The tissue of the valve achieves a higher tensile strength as a result of the tanning under pressure for greater life and assured performance. Furthermore, the process serves for quality control as valves exhibiting excess leakage can be detected and discarded. In the event that leakage past the cusps 20 of the valves 10 raises the level of the fluid 33 in the tank 22 too high, the excess is returned to the reservoir 26 by the pump 24.

In appearance, the prepared valve will resemble the illustration of FIG. 4 with a generally regular contour and coaptation of the cusps 20. The cusps are closed as in diastole, and the valve is in its normal physiologic state. Without the treatment in accordance with this invention, the valve may appear generally as shown in FIG. 5, with an uneven contour and the potential of leakage through the cusps.

The process of this invention as used in preparing arteries and veins for implantation may be seen in FIGS. 6 and 7. Here, one end of a vessel 35 is fitted over the downwardly extending stem 36 of a fluid manifold 37, held to it by means of sutures 38. The manifold 37 may be generally similar to the manifold 31 described above. The vessel 35 is received within a shallow tank 39 containing the tanning fluid 33. The other end 40 of the vessel 35 is ligated by sutures 41, and its collaterals 42 are ligated by sutures 43. This causes the vessel 35 to define an enclosed chamber. Within the interior of the vessel 35 is a straight rod 44, which extends the major part of the length of the vessel. The rod 44 is made of a suitable inert material, such as glass or a plastic such as polyolefin, and is of a constant outside diameter. The diameter of the rod 44 is less than that the vessel 35 assumes when it is under its normal physiologic pressure. The rod, however, serves to keep the vessel 35 straight under all conditions, this being the natural configuration for the vessel illustrated.

The manifold 37 is connected through a line 45 to an elevated reservoir of tanning fluid or other source of tanning fluid under pressure within the physiologic range. The internally applied tanning fluid inflates the vessel 35 so that during its period of fixation it assumes generally the normal diameter of a pressurized vessel. The tanning fluid in the tank 39 is applied to the exterior of the vessel 30 simultaneously to the internal pressurization with tanning fluid from the manifold 37. When treated in this manner, the vessel 35 has an improved shape, greater tensile strength and more uniformity of fixation with a greater penetration of the fixative than if conventional fixing procedures are followed.

The rod within the vessel need not be straight, but may be shaped to other contours to correspond to a desired overall configuration for the vessel. As shown in FIG. 8, the rod 46 is U-shaped, maintaining that contour for a vessel 47 which in its natural state has a different shape. Again, the end 48 of the vessel 47 is ligated as are its collaterals 49. The vessel is immersed in the tanning fluid 33 and attached to the manifold stem 36, as before. Pressure then is applied to the interior of the vessel during its period of fixation. When the tanning operation is complete, the vessel will retain substantially the U-shaped contour of the rod 46. This enables specially shaped natural vessels to be produced to suit particular requirements. The U-shaped vessel, for example, can be used as a shunt between vein and artery during kidney dialysis.

Instead of a rod within the vessel, a tube may be placed around the vessel to perform a similar function of maintaining it in a desired configuration. In FIG. 9 there is shown a U-shaped tube 50 of constant diameter surrounding a vessel 51, which has a natural shape differing from that of the tube. The tube 50 has a greater diameter than that of the vessel 51 before its interior is pressurized, as shown. However, pressurization of the vessel 51 will expand it to approach the lateral dimension of the tube 50. The tube 50 keeps the vessel 51 in the proper shape throughout the tanning process.

Other configurations of rod or tube may be devised to accommodate vessels to be fixed either in their natural shapes or in different shapes. Bifurcations, trifurcations and the like are possible utilizing a tube as the guiding element.

The foregoing detailed description is to be clearly understood as given by way of illustration and example only, the spirit and scope of this invention being limited solely by the appended claims.

We claim:

1. A device for preparing for implantation natural tissues in a form in which a portion thereof is subjected to pressure within the physiologic range when implanted comprising
    a tank,
    a quantity of tanning fluid in said tank,
    a reservoir at a predetermined height above said tank,
    a fluid conduit extending downwardly from said reservoir to a position adjacent said tank,
    means at the lower end of said conduit for engaging such tissues in said tank, and additional tanning fluid in said reservoir and said conduit for applying a pressure head to such tissues associated with said means at the end of said conduit for applying a predetermined pressure to such tissues.

2. A device as recited in claim 1 including addition guide means for engaging said tissues and maintaining said tissues substantially in a predetermined overall configuration while said tanning fluid is so applied to said tissues.

3. A device as recited in claim 2 in which said guide means is an elongated member adapted to be received within a chamber defined by such tissues.

4. A device as recited in claim 2 in which said guide means is a tubular member adapted to receive said tissues.

5. A device as recited in claim 2 in which said guide means is substantially U-shaped.

6. A device for preparing for implantation natural tissues in a form in which a portion thereof is subjected to pressure within the physiologic range when implanted comprising
    a tank adapted to receive such tissues,
    a quantity of tanning fluid in said tank,
    a source of said tanning fluid under a predetermined pressure,
    a fluid conduit extending from said source of said tanning fluid under a predetermined pressure to a portion of said conduit at said tank,
    and means at said portion of said conduit for association with such tissues in said tank for applying a predetermined pressure to such tissues.

7. A device as recited in claim 6 including in addition guide means for engaging said tissues and maintaining said tissues substantially in a predetermined overall configuration while said tanning fluid is so applied to said tissues.

8. A device as recited in claim 7 in which said guide means is an elongated member adapted to be received within a chamber defined by such tissues.

9. A device as recited in claim 7 in which said guide means is a tubular member adapted to receive said tissues.

10. A device as recited in claim 7 in which said guide means is substantially U-shaped.

* * * * *